United States Patent
Kopperschmidt

(10) Patent No.: US 8,715,214 B2
(45) Date of Patent: May 6, 2014

(54) METHOD AND DEVICE FOR FILLING A SUPPLY DEVICE OF A THERAPY APPLIANCE

(75) Inventor: Pascal Kopperschmidt, Dittelbrunn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1042 days.

(21) Appl. No.: 12/310,137

(22) PCT Filed: Aug. 23, 2007

(86) PCT No.: PCT/EP2007/007428
§ 371 (c)(1),
(2), (4) Date: Feb. 12, 2009

(87) PCT Pub. No.: WO2008/022792
PCT Pub. Date: Feb. 8, 2008

(65) Prior Publication Data
US 2010/0004579 A1 Jan. 7, 2010

(30) Foreign Application Priority Data
Aug. 24, 2006 (DE) .......................... 10 2006 039 675

(51) Int. Cl.
*A61M 37/00* (2006.01)
(52) U.S. Cl.
USPC ........................................ 604/6.07; 604/6.11
(58) Field of Classification Search
USPC ......... 604/4.01, 5.01, 6.07, 6.11, 82–86, 122, 604/123, 246
See application file for complete search history.

(56) References Cited

U.S. PATENT DOCUMENTS

| 4,252,118 | A | 2/1981 | Richard et al. |
|---|---|---|---|
| 5,015,226 | A | 5/1991 | Polaschegg |
| 5,116,316 | A * | 5/1992 | Sertic et al. ............. 604/83 |
| 5,411,490 | A | 5/1995 | Tennican et al. |
| 5,690,831 | A | 11/1997 | Kenley et al. |
| 5,755,692 | A * | 5/1998 | Manicom ............. 604/152 |
| 6,077,443 | A | 6/2000 | Goldau |
| 6,221,040 | B1 | 4/2001 | Kleinekofort |
| 6,526,357 | B1 * | 2/2003 | Soussan et al. ............ 702/45 |
| 2004/0035743 | A1 | 2/2004 | Tighe et al. |
| 2005/0096593 | A1 * | 5/2005 | Pope et al. ............ 604/122 |
| 2005/0234382 | A1 * | 10/2005 | Tonelli et al. ............ 604/4.01 |
| 2006/0054215 | A1 | 3/2006 | Remkes et al. |

FOREIGN PATENT DOCUMENTS

| CN | 1741826 A | 3/2006 |
|---|---|---|
| DE | 197 34 002 C1 | 9/1998 |
| DE | 198 48 235 C1 | 3/2000 |
| DE | 10302691 B3 | 4/2004 |
| JP | H05-506597 | 9/1993 |
| JP | H05-076446 | 10/1993 |
| JP | H5-76446 | 10/1993 |
| JP | 2004-508897 | 3/2004 |
| WO | WO 92/14509 | 9/1992 |
| WO | WO 96/09844 | 4/1996 |
| WO | WO 02/24259 | 3/2002 |
| WO | WO 2006/034178 | 3/2006 |

* cited by examiner

*Primary Examiner* — Philip R Wiest
(74) *Attorney, Agent, or Firm* — Jacobson Holman PLLC

(57) ABSTRACT

A method is provided for the filling of a metering apparatus of a therapy device having an extracorporeal circuit with which the metering apparatus is in communication such that an agent can be infused into the extracorporeal circuit during the operation of the therapy device by means of the metering device. The method includes a step of diluting a concentrate located in the metering apparatus by taking up a diluting agent from the extracorporeal circuit.

26 Claims, 1 Drawing Sheet

METHOD AND DEVICE FOR FILLING A SUPPLY DEVICE OF A THERAPY APPLIANCE

CROSS-REFERENCE TO RELATED APPLICATION

This is a national stage of PCT/EP2007/007428 filed Aug. 23, 2007 and published in German, which has a priority of German no. 10 2006 039 675.8 filed Aug. 24, 2006, hereby incorporated by reference.

BACKGROUND OF THE INVENTION

1. Field of Invention

The present invention relates to a method for the filling of a metering apparatus of a therapy device having an extracorporeal circuit with which the metering apparatus is in communication such that an agent can be infused into the extracorporeal circuit by means of the metering apparatus during the operation of the therapy device, with the method comprising the step of diluting a concentrate located in the metering apparatus with a diluting agent before the start of the patient treatment.

2. Description of the Prior Art

In extracorporeal blood treatment processes, anticoagulants, in particular heparin, are used to prevent blood clotting during the treatment.

The supply of the anticoagulant typically takes place via a syringe pump which delivers the anticoagulant directly into the extracorporeal blood circuit of a therapy device.

The heparin syringes to be inserted into the syringe pump, which typically have a volume of e.g. 30 ml, are first initially manually filled with a small amount of concentrated heparin by the dialysis staff in accordance with the prior art, said concentrated heparin then being diluted to the desired concentration by the manual metering of physiological saline.

The filling of the heparin pump thus typically takes place separately in accordance with the specifications of the physician and individually for each patient by the treatment staff before the filled syringe is connected to the blood hose system.

The treating staff has to manufacture the amount and concentration of the diluted heparin in the heparin syringe such that a specific dose can be dispensed in accordance with the medication at a specific delivery rate of the syringe pump. The different parameters to be observed must be converted or calculated manually by the staff, with this procedure as a rule taking place individually and separately for each patient before the start of treatment in accordance with the medication specified by the physician.

Consumables such as disposable gloves, a disposable syringe with needle for the transfilling of the concentrated heparin and a flask of physiological saline and disinfectant are required for each patient for the making available of the syringe filled with diluted heparin. The procedure takes several minutes in each case for each patient and is not only time-consuming, but, as stated, also prone to error.

It is known from the prior art that heparin syringes prefilled with a mixture of concentrated anticoagulant or of heparin and physiological saline are inserted into syringe pumps on dialysis machines and heparin is infused into the extracorporeal blood circuit, that is into the patient's blood, in accordance with a specific dose specification. Reference is to be made by way of example to U.S. Pat. No. 5,015,226 and to U.S. 2005/0234382 A1.

SUMMARY OF THE INVENTION

It is the object of the present invention to further develop a method of the type first mentioned such that the preparation of the metering apparatus is made more simple with respect to procedures known from the prior art.

This object is solved by a method having the features described herein. Provision is accordingly made that the dilution of the concentrate located in the metering apparatus takes place in that the metering apparatus accepts the diluting agent from the extracorporeal circuit in the condition connected to the extracorporeal circuit. It is not known from the prior art, for example, to draw up a heparin syringe directly on the extracorporeal blood circuit or to fill a heparin syringe on the extracorporeal blood circuit with a diluting agent, for example physiological saline. The prejudice rather applied in the prior art that a draw-up movement of a syringe at the extracorporeal blood circuit was generally prohibited.

The method in accordance with the invention has the advantages inter alia that the filling of the metering apparatus is comparatively simple, whereby the staff is relieved and can accordingly concentrate more on the patient. There is a time saving for the staff which ultimately results in a cost saving.

In another respect, increased safety is ensured since the comparatively complex preparation of the metering apparatus, for example of the syringe, such as is known from the prior art, is dispensed with.

It is particularly advantageous for the metering apparatus to be filled with a standardized amount and/or concentration of the concentrate. It is thus conceivable that, for example, syringes prefilled with a specific, standardized amount of concentrated heparin are inserted into the syringe pump. Before the start of the treatment, the concentrate in the prefilled syringe is diluted to the desired value by drawing up physiological saline from the extracorporeal blood circuit. If this procedure takes place in an automated manner, for example by the dialyzer, the manual workstep of the heparin dilution, such as is known from the prior art, and preferably also the conversion by the treatment staff required in this connection become superfluous, with the safety for the patient being increased and the amount of work for the staff being substantially reduced.

In a further aspect of the invention, provision is made for the metering apparatus to be a syringe pump with a syringe inserted therein and for the taking up of the diluting agent to take place by drawing up the syringe.

It is conceivable to provide the named standardized amount and/or concentration of the concentrate ex works so that the treatment center is supplied with correspondingly prefilled syringes. It is likewise generally conceivable to have the syringes prepared by the treatment staff in batches and to store them locally. As stated, a supply of syringes prefilled in a standard manner with heparin preparation by relevant syringe manufacturers is also conceivable. The invention is naturally not limited to the use of heparin. Any concentrate that has to be supplied to the patient's blood can be used within the framework of the invention.

In a further aspect of the invention, provision is made for the taking up of the diluting agent by the metering apparatus to take place during the flushing phase of the extracorporeal circuit and preferably briefly before the end of the flushing phase of the extracorporeal circuit.

Provision is made in a further aspect of the invention for the flushing of the extracorporeal circuit to take place with saline solution or with a dialysate preferably manufactured online and for the diluting agent accordingly to be saline solution or dialysate.

As stated above, the concentrate is preferably an anticoagulant and particularly preferably heparin.

In a further aspect of the invention, provision is made for a pressure sensor being in communication with the extracorporeal circuit to be arranged which takes over a monitoring of the pressure during the taking up of the diluting agent by the metering apparatus, with information to the user being given in the event of inconsistency between the fluid volume taken up by the metering apparatus and the measured pressure. This information can take place, for example, in the form of an alarm or of an acoustic or optical display. The pressure sensor can thus be used to detect leaks at the connection point between the extracorporeal blood circuit and a syringe or a hose running from the syringe to the extracorporeal blood circuit in a pressure-monitored manner.

In a further embodiment of the invention, input means are provided by means of which the concentration of the agent to be metered individually for the patient can be input, with a control unit being provided which determines the required volume of the diluting agent on the basis of the data received from the input means and controls the metering apparatus such that it takes up the specified volume of the diluting agent. It is, for example, conceivable that a medication individual for the patient can be read out from a card or from any other memory means by the therapy device or is transferred to the therapy device and that, on the basis of this information, the required volume of the diluting agent is calculated in an automated manner and is then taken up by means of the metering apparatus.

It is furthermore conceivable for the metering apparatus to be filled with one of a plurality of standardized amounts and/or concentrations of the concentrate and for the therapy device to have input means into which it can be input which of the standardized concentrates it is. The therapy device only has to have the heparin concentration communicated to it which was, for example, fixed ex works or on the part of a treatment center. A repeat input of a concentration is only necessary on the change of the filling of the prefilled syringes, but not on every treatment.

It is also possible to equip the heparin syringe with a detection feature so that the dialysis machine can automatically detect the properties of a heparin syringe with a supplier-side prefilling by means of known optical, mechanical or electronic means.

The therapy device is preferably a dialyzer.

The present invention furthermore relates to an apparatus, namely a therapy device, preferably a dialysis machine, which is suitable for the reception of an extracorporeal blood circuit, for example of a blood tubing set and/or of a cassette system. The therapy device has a metering apparatus for concentrate with a diluting agent. Provision is made in accordance with the invention for the therapy device to have a control unit and input means or to be in communication therewith, with the control unit determining the required volume of the diluting agent in an automated manner on the basis of the data received from the input means and controlling the metering apparatus such that it takes up the specified volume of the diluting agent from the extracorporeal blood circuit.

Further advantageous aspects of the therapy device are also described herein.

BRIEF DESCRIPTION OF THE DRAWING

Further details and advantages of the invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
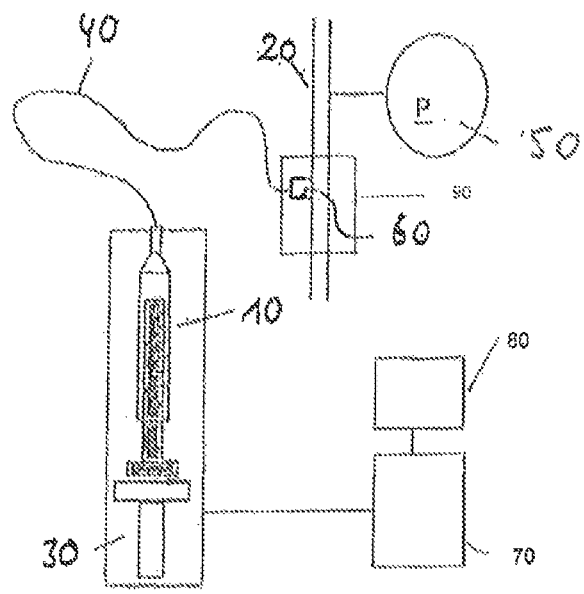
FIG. 1: a schematic representation of a syringe pump in communication with the extracorporeal blood circuit.

In accordance with a preferred embodiment of the present invention, the heparin syringe 10 visible from FIG. 1, which is prefilled with a heparin concentration fixed ex works, is connected to the tube system during the equipping of the blood hose system 20 for the carrying out of the therapy process/dialysis process and is inserted into the provided delivery unit, namely the syringe pump 30. During the flushing phase of the blood hose system 20 with physiological fluid, preferably with physiological saline, the syringe pump 30 is filled with the physiological fluid shortly before the end of the flushing until a defined heparin concentration in the syringe 10 is reached. For this purpose, the heparin concentration which is fixed ex works and is present in the syringe is communicated to the therapy device made as a dialyzer in accordance with this embodiment. The therapy device then calculates the required volume of the diluting agent with reference to the individually prescribed prescription for the patient and carries out a corresponding actuation of the syringe 10 in an automated manner such that the latter takes up the computed volume of physiological fluid from the extracorporeal blood circuit (i.e., blood hose system) 20 via the connection line 40. The prescribed concentration of the diluted heparin solution is then located in the syringe 10.

Furthermore, provision can be made for the therapy device to automatically calculate the delivery rate of the heparin pump with reference to an individually prescribed prescription for the patient and to add it to the blood to be therapied during the treatment in accordance with a defined profile.

In the following, a possible process routine for the carrying out of the method in accordance with the invention is presented:

The heparin dose is usually given in "units". Typical doses of heparin in dialysis treatments are around 500-1,000 units per hour. One-time initial does are 1,000 to 3,000 units. Heparin is provided in glass bottles of 5 ml with 25,000 units. A 30 ml large heparin syringe prefilled ex works could accordingly be filled with a selected dose of 10,000 units. This would correspond to a volume of 10,000/25,000*5 ml=2 ml. These heparin syringes can be prefilled ex works or in a fairly large number at the dialysis center.

The 30 ml heparin syringe 10 prefilled with 2 ml heparin is connected to the extracorporeal blood hose system 20 during preparation and is filled with fresh physiological flushing solution, e.g. dialysate, before the end of the flushing procedure. For example, the heparin syringe can be filled with 18 ml flushing solution so that a heparin concentration arises of 20,000 units/20 ml=1,000 units/ml. The filling of the 30 ml syringe on the machine side should not exceed the volume of 25 ml. If the prescription requires an initial dose of 2,500 units at the start of the treatment and a continuous dosage of 500 units per hour, the heparin pump 30 will add a bolus of 2.5 ml to the blood immediately after the start of the treatment. The heparin syringe will continuously supply a delivery rate of 0.5 ml per hour up to the desired stop time.

As can furthermore be seen from FIG. 1, a pressure sensor 50 is connected to the extracorporeal blood hose system, said pressure sensor being able to be the pressure sensor anyway present in the arterial blood hose line. The sensor 50 serves for the monitoring of the filling of the syringe 10 within the framework of the method in accordance with the invention. During the drawing up of the syringe 10 for the reception of the diluting agent from the blood hose system 20, the pressure is monitored by means of the sensor 50. If an inconsistency is found between the pressure drop and the filling of the syringe 10, this can be communicated accordingly to the user. In this manner, the tightness can be checked and leaks at the connection point 60 between the connection hose 40 and the extracorporeal blood hose system 20 can be pressure-monitored. The filling can be taken from a saline bag or from a dialysate prepared online in accordance with the flushing procedure.

As shown in FIG. 1, the invention also includes an input device 80 with which the concentration of the agent to be metered can be input individually for a specific patient, and a control unit 70 which (i) determines the required volume of the diluting agent in an automated manner on the basis of the data received from the input device 80 and (ii) controls the metering apparatus, i.e., the syringe 10, such that the syringe takes up the determined volume of the diluting agent.

Instead of the blood hose system 20, the heparin syringe 10 can also be connected to a cassette system 90 as shown in FIG. 1.

The term of the extracorporeal circuit within the framework of the present invention comprises, for example, the blood hose system, the cassette system, etc. or any other constituents and components of the extracorporeal circuit.

Figure 2:
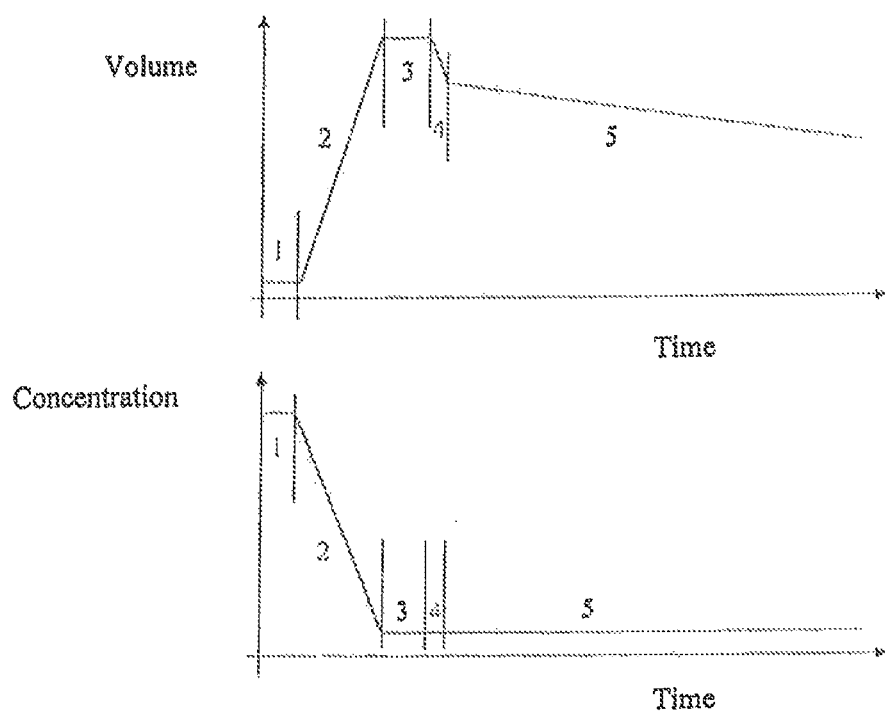
FIG. 2: the time procedures of the volume and of the concentration of a heparin solution in a heparin syringe.

FIG. 2 shows the time procedure of the volume located in the syringe 10 (upper illustration) and the time procedure of the heparin concentration of the heparin solution located in the syringe 10 (lower illustration).

The time zones in detail designate the equipping phase 1, the filling of the syringe 2, connection of the patient 3, adding of the heparin bolus 4 and continuous heparin dosing during the treatment 5.

In accordance with the prescription of the physician, the initial dose is communicated to the therapy device in heparin "units", the continuous dosage in "units per hour" and the profile and the stop time by input or patient card. The input of the concentration in the heparin syringe filled ex works is only necessary on a change in the filling of the prefilled syringes, but not before every treatment.

The concentration of heparin is determined in accordance with the filling of the heparin syringe ex works and the initial volume and the delivery rate are determined in accordance with the specifications of the physician via simple relationships.

The following computation steps are carried out, by way of example, on the device side:

Concentration of the syringe filled with 25 ml:

$$c_{Hep} = \frac{10.000 \text{ Units}}{25 \text{ ml}} = 400 \frac{\text{Units}}{\text{ml}}$$

Initial volume with an additional dosage of 2,000 units:

$$V_{initHep} = \frac{2.000 \text{ Units}}{c_{Hep}} = 5 \text{ ml}$$

Continuous delivery rate with a dosage of 500 units per hour:

$$Q_{Hep} = \frac{500 \text{ Units}}{h} \cdot \frac{1}{c_{Hep}} = 1{,}25 \frac{\text{ml}}{h}$$

In accordance with the embodiment shown here by way of example, the advantage is achieved that a conversion of a dosage of heparin prescribed for a specific patient from "units" into "ml per hour" is omitted. The required computation steps can be carried out on the device side. Computation errors can thereby be reliably avoided. The delivery rate of the heparin pump is then irrelevant for the staff and their attention can be reduced solely to the prescribed dosage in the "units".

As was stated above, the advantage results due to the use of heparin prefilled ex works or at the dialysis center that the filling with an individualized amount of heparin matched to the patient and the use of additional consumable materials are omitted. The process procedure is substantially simplified with respect to the solutions known from the prior art due to the filling of the metering apparatus or syringe from the extracorporeal blood circuit during the preparation phase. A further advantage results from the fact that connection points and inlet lines can simultaneously be checked for tightness and passage on the device side, for which purpose the aforesaid pressure sensor can be used. A saving in consumable material and so a cost advantage result from the standardized preparation of heparin syringes. The method in accordance with the invention is preferably carried out automatically. This means an intervention of the user is preferably not necessary.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of filling a metering apparatus of a therapy device having an extracorporeal circuit with which the metering apparatus is in communication such that an agent can be introduced into the extracorporeal circuit with the metering apparatus during operation of the therapy device, the method comprising:
a step of diluting a concentrate located in the metering apparatus by taking up a diluting agent from the extracorporeal circuit with which the metering apparatus is in communication, said taking up of the diluting agent by the metering apparatus occurring during a flushing of the extracorporeal circuit.

2. The method in accordance with claim 1, wherein the metering apparatus is filled with at least one of a standardized amount and a standardized concentration of the concentrate.

3. The method in accordance with claim 1, wherein the metering apparatus is a syringe pump with a syringe inserted therein, and wherein the taking up of the diluting agent is effected by drawing up the syringe.

4. The method in accordance with claim 1, wherein the diluting agent is a saline solution or a dialysate, and wherein the flushing of the extracorporeal circuit is effected with the saline solution or the dialysate.

5. The method according to claim 4, wherein the saline solution or the dialysate is prepared online.

6. The method in accordance with claim 1, wherein the concentrate is an anticoagulant.

7. The method in accordance with claim 6, wherein the anticoagulant is heparin.

8. The method in accordance with claim 1, wherein the therapy device includes a pressure sensor in communication with the extracorporeal circuit, and the method further comprising a step of monitoring pressure measured by the pressure sensor during the taking up of the diluting agent by the metering apparatus such that should an inconsistency arise between a fluid volume taken up by the metering apparatus and the measured pressure, the inconsistency is detected.

9. The method in accordance with claim 1, wherein the therapy device includes an input device with which a concentration of the agent to be metered can be input individually for a patient and
   a control unit which determines a required volume of the diluting agent in an automated manner based on data received from the input device, and which controls the metering apparatus such that it takes up a determined volume of the diluting agent.

10. The method in accordance with claim 9, wherein the input device includes a reading device with which a medication specific to an individual patient can be read out from a card or from another memory device.

11. The method in accordance with claim 1, wherein the metering apparatus is filled with one of a plurality of at least one of standardized amounts and concentrations of the concentrate, and wherein the therapy device includes an input device into which an identity of the standardized concentrate can be input.

12. The method according to claim 1, wherein the taking up of the diluting agent by the metering apparatus occurs briefly before an end of the flushing of the extracorporeal circuit.

13. A therapy device configured for taking up a diluting agent from an extracorporeal circuit, comprising:
   a metering apparatus for concentrate that includes the diluting agent; and
   a control unit and an input device, with the control unit being configured to (i) determine a required volume of the diluting agent in an automated manner based on data received from the input device and (ii) control the metering apparatus to take up the determined volume of the diluting agent from the extracorporeal circuit during a flushing of the extracorporeal circuit.

14. The therapy device in accordance with claim 13, wherein the metering apparatus is filled with a standardized amount and concentration of the concentrate.

15. The therapy device in accordance with claim 13, wherein the metering apparatus is a syringe pump having a syringe inserted therein, with the metering apparatus being arranged such that the taking up of the diluting agent from the extracorporeal circuit is effected by drawing up the syringe.

16. The therapy device in accordance with claim 13, wherein the diluting agent is a saline solution or a dialysate, and wherein the extracorporeal circuit is flushed with the saline solution or the dialysate.

17. The therapy device according to claim 16, wherein the saline solution or the dialysate is prepared online.

18. The therapy device in accordance with claim 13, wherein the concentrate is an anticoagulant.

19. The therapy device in accordance with claim 18, wherein the anticoagulant is heparin.

20. The therapy device in accordance with claim 13, further comprising
   a pressure sensor in communication with the extracorporeal circuit;
   a monitoring device that monitors pressure measured by the pressure sensor during the taking up of the diluting agent by the metering apparatus; and
   an information device that, should an inconsistency arise between a fluid volume taken up by the metering apparatus and the measured pressure, provides information to a user of the therapy device.

21. The therapy device in accordance with claim 13, wherein the input device can be input with concentrations of the agent to be metered for an individual patient.

22. The therapy device in accordance with claim 13, wherein the input device includes a reading device from which a medication specific to a patient can be read off from a card or from another memory device.

23. The therapy device in accordance with claim 13, wherein the metering apparatus is filled with one of a plurality of at least one of standardized amounts and concentrations of the concentrate, and wherein the therapy device includes an input device into which an identity of the standardized concentrate can be input.

24. The therapy device in accordance with claim 13, wherein the extracorporeal circuit includes at least one of a blood tubing set and a cassette system.

25. The therapy device according to claim 13, wherein the therapy device is a dialysis machine.

26. The therapy device according to claim 15 13, wherein the taking up of the diluting agent by the metering apparatus occurs briefly before an end of the flushing of the extracorporeal circuit.

* * * * *

UNITED STATES PATENT AND TRADEMARK OFFICE
CERTIFICATE OF CORRECTION

PATENT NO. : 8,715,214 B2  Page 1 of 1
APPLICATION NO. : 12/310137
DATED : May 6, 2014
INVENTOR(S) : Pascal Kopperschmidt It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1004 days.

Signed and Sealed this
Twenty-ninth Day of September, 2015

Michelle K. Lee
*Director of the United States Patent and Trademark Office*